United States Patent
Metzler et al.

(10) Patent No.: US 7,863,015 B2
(45) Date of Patent: Jan. 4, 2011

(54) METHOD AND DEVICE FOR CARRYING OUT BIOCHEMICAL REACTIONS WITH A HIGH THROUGHPUT

(75) Inventors: Thomas Metzler, Munich (DE); Hans Schels, Munich (DE); Rolf Reichhuber, Penzberg (DE); Jochen Kluge, Munich (DE)

(73) Assignee: Roche Diagnostics GmbH (DE)

( * ) Notice: Subject to any disclaimer, the term of this patent is extended or adjusted under 35 U.S.C. 154(b) by 1005 days.

(21) Appl. No.: 11/224,719

(22) Filed: Sep. 12, 2005

(65) Prior Publication Data

US 2006/0008899 A1    Jan. 12, 2006

Related U.S. Application Data (63) Continuation of application No. 10/722,715, filed on Nov. 25, 2003, now abandoned, which is a continuation of application No. 09/763,077, filed as application No. PCT/EP00/05378 on Jun. 10, 2000, now abandoned.

(30) Foreign Application Priority Data

Jun. 18, 1999   (EM) ............................... 99 111 762

(51) Int. Cl.
*C12M 1/12* (2006.01)
*C12M 1/40* (2006.01)
*C12P 21/00* (2006.01)

(52) U.S. Cl. ................ 435/68.1; 435/297.1; 435/297.5; 422/101; 422/102; 210/321.71; 210/321.75

(58) Field of Classification Search ............. 435/297.1, 435/297.5, 301.1, 68.1, 297.2; 422/101, 422/102; 210/321.71, 321.72, 321.75; 73/38, 73/64.47
See application file for complete search history.

(56) References Cited

U.S. PATENT DOCUMENTS 3,275,528 A   9/1966   Ainis (Continued)

FOREIGN PATENT DOCUMENTS

DE       4237113 A1   5/1994

(Continued)

OTHER PUBLICATIONS

Machine translation of DE 3723004 (Jan. 1989).*

(Continued)

*Primary Examiner*—William H Beisner
(74) *Attorney, Agent, or Firm*—Barnes & Thornburg LLP (57) ABSTRACT

Device, method and kit for carrying out biochemical reactions, in particular for cell-free polypeptide biosynthesis composed of an external housing which encloses an inner housing with incorporated wells and a supply chamber, wherein the wells of the inner housing each contain a producing system during the biochemical reaction, the supply chamber contains a supply liquid during the biochemical reaction and the wells of the inner housing and the supply chamber are separated by a semipermeable membrane characterized in that the inner housing has at least two wells the lower ends of which are closed by a semipermeable membrane and the upper ends of which protrude from the supply liquid contained in the supply chamber, and is connected to means for moving and incubating the producing systems and to the supply liquid.

15 Claims, 4 Drawing Sheets

U.S. PATENT DOCUMENTS

| | | | |
|---|---|---|---|
| 3,623,611 | A | 11/1971 | Riley et al. |
| 4,450,076 | A | 5/1984 | Medicus et al. |
| 4,642,220 | A | 2/1987 | Bjorkman |
| 5,362,624 | A | 11/1994 | Schmitt et al. |
| 5,462,874 | A * | 10/1995 | Wolf et al. ............... 435/297.5 |
| 5,478,730 | A | 12/1995 | Alakhov et al. |
| 5,506,121 | A | 4/1996 | Skerra et al. |
| 5,593,856 | A | 1/1997 | Choi et al. |
| 5,602,028 | A | 2/1997 | Minchinton |
| 5,614,205 | A * | 3/1997 | Usala ..................... 424/424 |
| 5,733,442 | A * | 3/1998 | Shukla ..................... 210/94 |
| 5,948,624 | A | 9/1999 | Rothschild et al. |
| 6,107,055 | A | 8/2000 | Bauer et al. |
| 6,242,247 | B1 * | 6/2001 | Rieser et al. ............. 435/297.1 |

FOREIGN PATENT DOCUMENTS

| | | |
|---|---|---|
| EP | 3723004 A1 | 1/1989 |
| EP | 0894852 A2 | 2/1999 |
| WO | 97/04074 | 2/1997 |
| WO | 99/50436 | 10/1999 |

OTHER PUBLICATIONS

Dong-Myung Kim et al., "A Semicontinuous Prokaryotic Coupled Transcription/Translation System Using a Dialysis Membrane," *Biotechnol. Prog.*, 1996, 12, 645-*649, 1996 American Chemical Society and American Institute of Chemical Engineers.

Patent Abstracts of Japan, Sainikusu: KK; "Incubator for trace Specimen," Publication No. 09322755, Publication Date Dec. 16, 1997, European Patent Office (1 pp).

Bartlett, A.J. et al., "The Radioimmunoassay of Buprenorphine," *Eur. J. Clin. Pharmacol.*, 18, 339-345 (1980).

Beike, J. et al., "A Specific Immunoassay for the Determination of Morphine and its Glucoronides in Human Blood," *Int. J. Legal Med.*, (1998), 112:8-14.

Debrabandere, L. et al., "Development of a Fluoroimmunoassay for the Detection of Buprenorphine in Urine," Mar. 1995, pp. 250-253.

Polettini, Aldo et al., "Simultaneous Determination of Buprenorphine, Norbuprenorphine, and Buprenophine-glucoronide in Plasma by Liquid Chromatography-Tandem Mass Spectrometry," *Journal of Chromatography B.*, 754 (2001), 447-459.

Subassinghe, K.R. et al., "Non-CNS Acting Opiates Bearing Guanidino Substituents," *Aust. J. Chem.*, (2004) 57, 427-438.

* cited by examiner

METHOD AND DEVICE FOR CARRYING OUT BIOCHEMICAL REACTIONS WITH A HIGH THROUGHPUT

CROSS-REFERENCE TO RELATED APPLICATIONS

This application is continuation of U.S. Ser. No. 10/722,715 filed Nov. 25, 2003, now abandoned which is a continuation of U.S. Ser. No. 09/763,077 filed Aug. 30, 2001, now abandoned, which claims priority to PCT/EP00/05378 filed Jun. 10, 2000, which claims priority to European Patent Application No. 99111762.3, filed Jun. 18, 1999, all of which are herein incorporated by reference

BACKGROUND

The invention concerns a method and a device for carrying out biochemical reactions especially for polypeptide biosynthesis and for the coupled in vitro transcription and translation of proteins in a cell-free system using a multi-channel dialysis device which enables the concurrent synthesis of different proteins in adequate yields under simple and reproducible conditions.

The principle of cell-free in vitro protein biosynthesis using dialysis membranes has been known for several years and essentially comprises two separate chambers (one for the reaction mixture, one for the supply solution) that are connected via a membrane with a suitable pore size. Protein synthesis takes place in the reaction chamber. The supply chamber contains a solution of all reaction components required for transcription or translation that are consumed in the reaction mixture during the process of protein biosynthesis. Due to the fact that both chambers are connected by a semipermeable membrane, consumed reaction components in the reaction chamber can be continuously replaced by new components from the supply chamber, if necessary by means of an appropriate pumping device, and consequently synthesis can be maintained over a considerably longer time period compared to a static system i.e. a corresponding reaction that takes place in a reaction vessel that is not subdivided. Corresponding methods for cell-free in vitro biosynthesis based on the continuous flow or the continuous exchange principle are described for example in U.S. Pat. No. 5,478,730, EP 0 593 757 and by Spirin et al. in Science vol. 242, 1988 p. 1162-1164.

The synthesis system used according to the document U.S. Pat. No. 5,478,730 for example contains a source of DNA or mRNA which codes for the polypeptide. In addition the cell-free synthesis system essentially contains ribosomes, tRNA, amino acids, ATP, GTP, UTP and CTP. The transcription of DNA and the translation of mRNA with the aid of tRNA results in the production of the respective polypeptide together with low molecular weight by-products and waste materials. These can pass into a supply space through a semipermeable membrane which segregates the space containing the synthesis system from the supply space. The supply space contains a liquid which acts as a supply medium containing in particular ATP, GTP and amino acids. These components are supplied to the synthesis system through the semipermeable membrane in order to replenish materials consumed during the biosynthesis reaction. Passage through the semipermeable membrane is possible since their molecular weight is below the cut-off limit. At the same time products of the biochemical reaction and other substances with a molecular weight below the cut-off of the barrier pass from the reaction space into the supply space. According to the U.S. Pat. No. 5,478,730 the semipermeable membrane is for example an ultrafiltration membrane in the form of hollow fibre membranes.

The U.S. Pat. No. 5,478,730 contains extensive additional information on suitable compositions for the synthesis system and the supply liquid. To this extent the present invention makes reference to the prior art and in particular this U.S. patent document and the literature references cited therein. The contents thereof are incorporated into the present application by way of reference.

The European Patent 0 593 757 describes the application of coupled transcription and translation for corresponding in vitro biosynthesis methods in which essentially an RNA polymerase was additionally added to the reaction mixture.

In addition various dialysis devices and membranes are known. The main distinction is between so-called single tube and multi-channel designs. The previously described and commercially available dialysis materials that are suitable for in vitro protein biosynthesis are exclusively based on the single tube principle (e.g. EP 99 91 01 418.4; Promega Notes 1997). These dialysis aids do not enable a high throughput or the concurrent synthesis of different proteins especially without complicated purification procedures or other measures such as the denaturation of proteins that are synthesized as inclusion bodies. An additional disadvantage of dialysis devices based on the single tube principle is that they are technically difficult to operate and time consuming.

Furthermore microtitre plates containing wells which are provided with a porous membrane at the lower end are commercially available. So-called multi-channel versions are only suitable for cell culture applications or for filtration or rebuffering processes (e.g. ultra-filtration membranes from Milipore; Slide-A-Lyzer® MINI Dialysis Unit from Pierce). However, these multi-channel devices do not allow an exchange of liquids of different concentrations that are used for in vitro transcription or in vitro translation which is why they are unsuitable for in vitro protein synthesis applications with for example a continuous supply and removal of components.

SUMMARY OF THE INVENTION

Hence the object of the invention is to provide a method and device which enable biochemical reactions to be carried out with high efficiency and at the same time in a simple and very reproducible manner.

The object is achieved by a device for carrying out biochemical reactions, in particular for cell-free polypeptide biosynthesis and/or for the production of biologically active proteins with a native structure composed of an external housing which encloses an inner housing with incorporated wells and a supply chamber, wherein the wells of the inner housing each contain a producing system during the biochemical reaction, the supply chamber contains a supply liquid and the wells of the inner housing and the supply chamber are separated by a semipermeable membrane characterized in that the inner housing has at least two wells the lower ends of which are closed by a semipermeable membrane and the upper ends of which protrude out of the supply liquid contained in the supply chamber, and is connected to means for moving and incubating the producing systems and the supply liquid.

DESCRIPTION OF THE INVENTION

Figure 3:
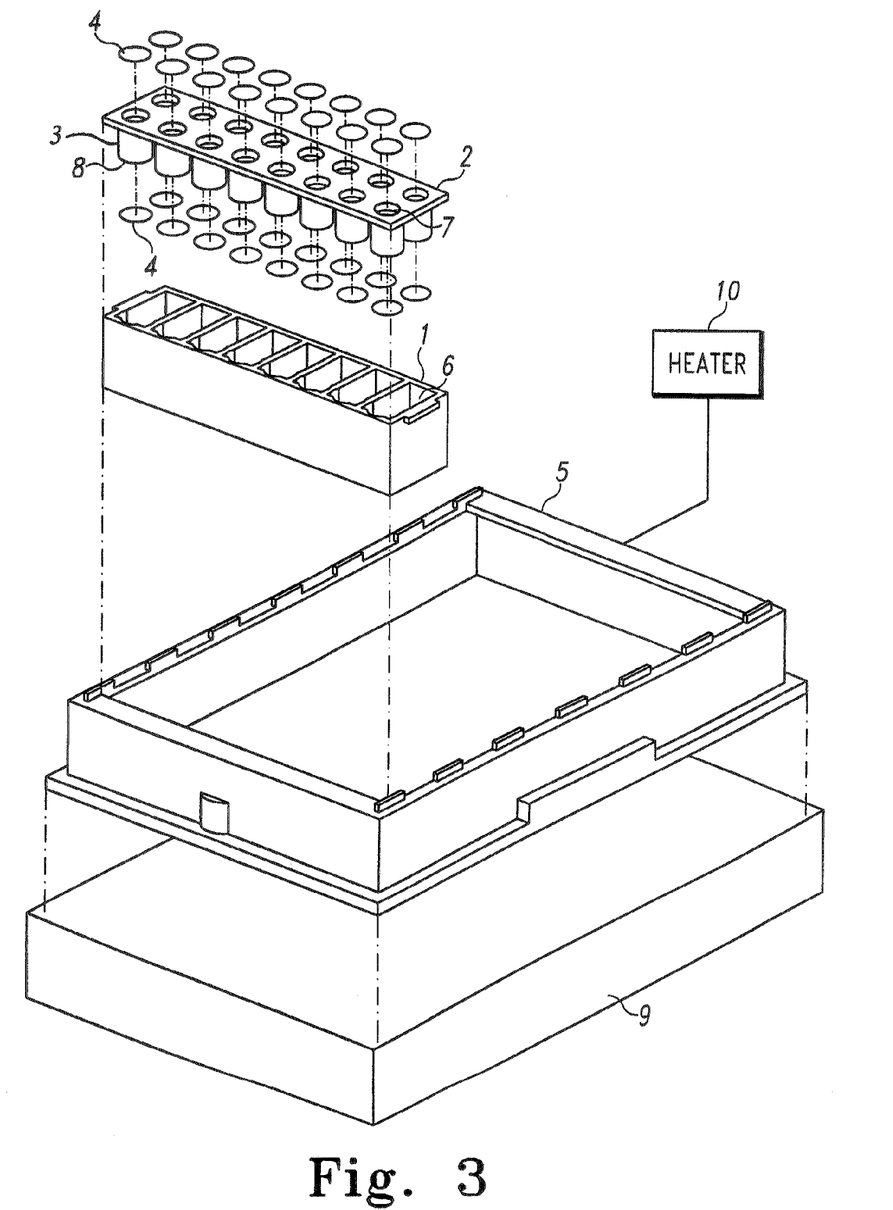
FIG. 3 is a drawing illustrating the particular features of one embodiment of the present invention wherein 1 and 2 are an inner housing (unassembled), 3 is a well comprising a side wall 7, 4 is a membrane closing the top opening and the lower end 8 of the well. A supply chamber, 6 is provided for receiving the wells, 3 wherein the supply chamber, 6 fits within an external housing, 5. The external housing, 5 is functionally linked to mixing means (9; e.g., a shaking device) for moving the external housing. Incubation means (10; e.g., a heater) are provide for heating samples contained in the wells (3) when the device is assembled.
Figure 4:
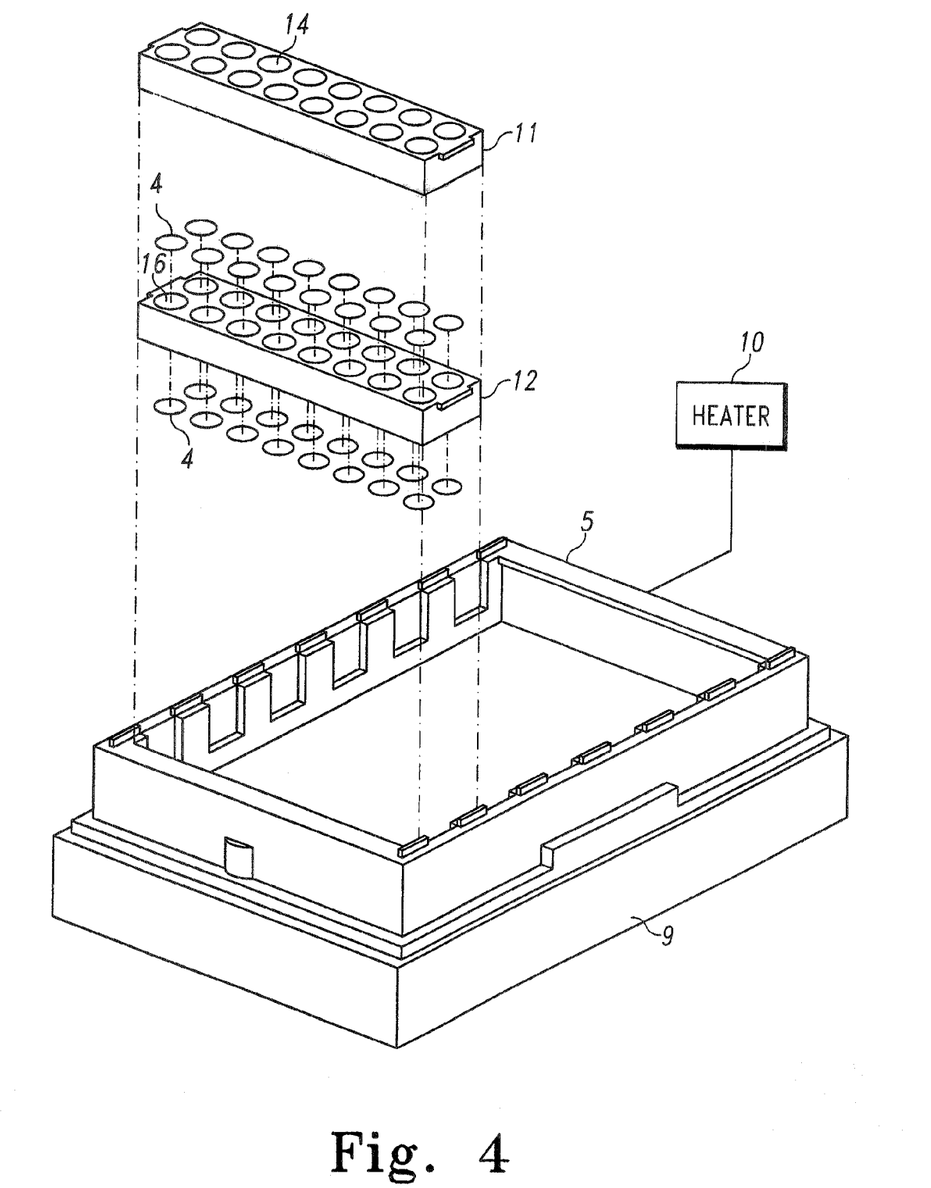
FIG. 4 is a drawing illustrating the particular features of one embodiment of the present invention wherein the device comprises a supply block (11) having a plurality of chambers (14) formed therein, a reaction block (12) having a plurality of chambers (16) formed therein, and a plurality of semipermeable membranes (4) attached to the top and bottom of the reaction block chambers (16). An external housing is formed for receiving the supply block (11) and reaction block (12) and is further provided with mixing means (9; e.g., a shaking device) for moving the external housing. Incubating means (10; e.g., a heater) are provided for heating samples contained in the reaction block chambers (16) when the device is assembled.

The present invention relates to a device for carrying out biochemical reactions, in particular for cell-free polypeptide biosynthesis and/or for the production of biologically active proteins with a native structure composed of an external housing 5 which encloses an inner housing 1, 2 with incorporated wells 3 and a supply chamber 6, wherein the wells of the inner housing each contain a producing system during the biochemical reaction, the supply chamber contains a supply liquid and the wells of the inner housing and the supply chamber are separated by a semipermeable membrane 4 characterized in that the inner housing has at least two wells the lower ends of which are closed by a semipermeable membrane and the upper ends 8 of which protrude out of the supply liquid contained in the supply chamber, and is connected to means for moving and incubating the producing systems and the supply liquid.

Suitable external housings for the invention are for example bowl-shaped or cylindrical vessels that are able to hold liquids and in which it is possible to insert and optionally fix a geometrically smaller inner housing. The inner housing can have any external dimensions which correspond in size and shape to the external housing. For example round, rectangular or quadratif designs are suitable for the external housing with volumes of ca. 10 ml to several liters. It is advantageous when the geometry of the inner housing conforms to that of the outer housing as far as possible. Furthermore the inner housing can have a microtitre plate (MTP) format. This enables a simple automation and acceleration of the individual operating steps.

The inner housing has one or several wells preferably two or more e.g. six, eight, twelve, 24, 48, 64, 96, 384 etc. However, in principle it is also possible to use an inner housing for the device according to the invention with several hundred to thousand or more wells for example in the form of blocks or microtitre plates. The wells are usually made of an inert material such as polyethylene or polypropylene and can be designed for volumes of ca. 50 μl up to several milliliters i.e. in the order of magnitude of 10 ml. Conical wells whose lower end is closed with a semipermeable membrane e.g. a dialysis membrane with a pore size of 3 to 100 kilo-daltons are advantageous. In principle all conventional dialysis and ultrafiltration membranes of a suitable pore size can be used for the invention. Dialysis membranes with a pore size of ca. 10 to 14 kilodaltons have proven to be particularly suitable. This enables the separation especially of interfering low-molecular inhibitory substances that are formed during the in vitro biosynthesis. Either each individual well or all wells together can be provided with a cap closure or foil to seal the upper openings of the wells i.e. the part of the wells of the inner housing which protrude from the supply liquid contained in the supply chamber. Alternatively a closing cap can also be attached to seal the entire outer housing.

A further preferred embodiment of the inner housing of the device according to the invention is composed of a layer of blocks with a plurality of drilled holes. A further flat block having the same hole geometry is located above a first block. A filter or semipermeable membrane is placed between the two blocks. The second flatter block is suitable for collecting by-products or waste materials which hence do not reach the supply chamber or only to a very slight extent. The end result is an inner housing with wells which are each divided by a membrane into a reaction space and a so-called second supply or dialysis chamber. Closing both sides of the inner housing with dialysis membranes, on the one hand, doubles the area available for exchange and, on the other hand, results in there being hardly any change in the volume of the samples. A particular advantage of this embodiment is that there is considerably less or delayed accumulation of non-utilizable components in the supply liquid sustaining the in vitro protein synthesis which further increases the efficiency of the protein synthesis.

Furthermore it has proven to be advantageous to coat the walls 7 of the individual wells of the inner housing with components that specifically bind the proteins and peptides synthesized in vitro. Suitable components are especially those that are suitable for the purification of tag-containing proteins. The protein synthesized in vitro in the wells (containing tag) can thus be bound in this manner to the coated microtitre plate and subsequently be directly purified, optionally after washing with suitable buffers or be eluted in a pure form by suitable reagents. An example of a so-called protein tag is Strep-Tag II (8AA sequence, see DE 42 37 113) which can be bound either to the N- or C-terminus of the in vitro synthesized protein. Streptactin, streptavidin or avidin can for example be used as coating substances. Processes for coating suitable surfaces are known to a person skilled in the art. Alternatively it is also possible to separate the synthesized, tag-carrying proteins from the reaction mixture of the individual wells by means of appropriately coated glass or magnetic particles.

The inventive device is additionally equipped with a stirring or shaking device in order to ensure an adequate movement or diffusion of the reaction solution(s) and the supply solution. It has proven to be advantageous to place a stirring element in the form of a magnetic stirrer in the supply chamber and optionally in each individual well in which a reaction proceeds. This ensures a simultaneous mixing of the producing system, of the mixtures in the individual wells and of the surrounding supply solution. In order to ensure a constant temperature during the biochemical reaction—which is usually between 20° and 37° C.—the entire device is most simply placed completely in a closable incubator or held under a temperature-controlled incubation hood. Moreover combined shaking or stirring and thermostating devices can be used according to the invention. The mixing of the reaction mixture(s) and of the supply solution can thus occur simultaneously with shaking or stirring movements of a suitable frequency and can be carried out over a long period at a constant temperature.

As a rule it is sufficient to incubate the reaction mixture(s) over a period of ca. 20 hours in order to obtain the desired proteins or peptides in adequate yields. Ca. 25 to 50 μg protein/250 μl reaction solution in a well which corresponds to a concentration of 100 to 200 μg/ml can already be reached after ca. 6 hours depending on the protein to be synthesized, the optimization of the individual process parameters and the exact composition of the supply solution. Moreover longer incubation times can lead to correspondingly better yields, for example concentrations of up to 500 μg/ml were obtained for GFP (green fluorescent protein). A further preferred embodiment of the invention is when the volume of the supply solution is determined according to the number or the total volume of the wells of the inner housing. As a guideline according to the invention the volume of the supply solution is equal to the sum of the number of wells and the volume per well multiplied by a factor of 10.

The composition of the supply solution essentially corresponds to that of corresponding solutions of the prior art for cell-free in vitro biosynthesis. Moreover a person skilled in the art will know that supply solutions for cell-free protein synthesis are subject to certain conventional optimization measures which especially depend on the type and quality of the ribosomal fraction i.e. whether for example a eukaryotic or prokaryotic system is used as the basis for the cell-free in vitro biosynthesis. In addition it has proven to be advantageous for the supply solution to contain an agent that reduces sulfide groups and—in the case of an *E. coli*-based lysate—an inhibitor for *E. coli* polymerases and optionally one or several suitable bactericidal substances.

A particularly preferred supply solution according to the invention for a coupled transcription/translation reaction contains in a suitable buffer system such as e.g. Hepes, ca. 150 to 400 mM potassium ions, ca. 10 to 50 mM magnesium ions, adequate amounts of the four nucleotide triphosphates (ATP, CTP, GTP and UTP) and all naturally occurring amino acids, ca. 20 to 80 mM acetyl phosphate, dithiothreitol as a reagent reducing sulfide groups and optionally EDTA, glycerol, one or several bactericidal substances such as e.g. rifampicin or sodium azide and preferably—in the case of a ribosomal fraction derived from *E. coli*—an RNA polymerase inhibitor such as rifampicin to deactivate *E. coli* polymerases. A typical reaction mixture for a transcription/translation reaction contains the appropriate components in comparable amounts to the supply solution. In addition a reaction mixture according to the invention contains the respective eukaryotic or prokaryotic ribosomal fraction such as e.g. an *E. coli* lysate, the DNA coding for the desired protein in the form of a plasmid, ca. 1 to 10 U/μl of an RNA polymerase, ca. 200 to 800 μg/ml of a tRNA and optionally further auxiliary substances such as RNase inhibitors.

An additional subject matter of the invention is a method for carrying out one and in particular several concurrent biochemical reactions using the device according to the invention wherein the supply liquid in the supply chamber is not subjected to an external applied pressure during the biochemical reaction and thus the molecular exchange between the supply chamber and the solutions of the individual wells of the inner housing is essentially based on diffusion. The method according to the invention and the device suitable therefore are particularly suitable for automated applications with a high synthesis throughput.

The invention additionally concerns a reaction kit for carrying out in vitro protein syntheses or for the coupled in vitro transcription and translation of proteins in a cell-free system using a corresponding device. The kit is essentially composed of a supply solution and a solution for the reaction mixtures. The solutions can be present in a liquid form as well as in a freeze-dried state. The supply solution essentially comprises a substance buffering between pH 7 and 8, ca. 150 to 400 mM potassium ions, ca. 10 to 50 mM magnesium ions, nucleotide triphosphates (ATP, CTP, GTP and UTP), ca. 20 different amino acids and a substance reducing sulfide groups. Moreover additional auxiliary substances such as stabilizers or inhibitors for preventing undesired reactions can be added to the supply solution. The solution for the reaction mixtures corresponds to the solution of the aforementioned supply solution and additionally contains a cell-free lysate i.e. a prokaryotic or eukaryotic ribosAmal fraction, tRNA and an RNA polymerase the origin of which is different from that of the ribosomal fraction. According to the invention it is preferable to not admix the components of the reaction mixture solutions that are different from the components of the supply solution until shortly before carrying out the reaction i.e. they are each present in separate vessels. This applies correspondingly to the supply solution as well as to the energy-rich compounds that are to be added to the reaction solution such as acetyl phosphate. This further improves the storage life and the adaptability of the reaction kit.

The invention is further illustrated by the following examples.

EXAMPLES

The method according to the invention for cell-free protein biosynthesis is elucidated in more detail in the following using an *E. coli* lysate and two model proteins (CAT and GFP):

Cell-free protein biosynthesis is carried out in the form of a coupled transcription and translation in which the mRNA to be transcribed is coded on a plasmid whose gene sequence contains a promoter for a viral RNA polymerase (e.g. SP6, T3 or T7 RNA polymerase). The mRNA transcribed in vitro is translated into the corresponding protein with the aid of the *E. coli* lysate present in the coupled system.

A. Reaction Components

Plasmids: pM-GFP or pIVEX-GFP contain the sequence for the green fluorescent protein from *Aequorea victoria* in the form of a mutant GFPcycle3 (27 kilo-daltons) (Nature Biotechnology, 1996, 14, p. 315-319); the coding region of the GFPcycle3 mutant was cloned into pTU58 instead of the wild type GFP sequence (Science, 1994, 263, 802). pHM-CAT contains the sequence for the chloroamphenicol acetyl transferase protein (22.5 kilodaltons). Construction: An insert (NcoI-BamHI) from pCAT3 (Promega) was inserted into pHM19 (FU Berlin, "Instit. f. Biochemie", Dr. Stiege).

*E. coli* S30 lysate: The lysate was prepared from an *E. coli* A19 strain by a modified method according to Zubay (Annu. Rev. Genet. 7, 267, 1973).

Lysate buffer: 100 mM Hepes-KOH pH 7.6/30° C., 14 mM magnesium acetate, 60 mM potassium acetate, 0.5 mM dithiothreitol Transcription/translation reaction mixture: 185 M potassium acetate, 15 mM magnesium acetate, 4% glycerol, 2.06 mM ATP, 1.02 mM CTP, 1.64 mM GTP, 1.02 mM UTP, 257 μM of each amino acid (a total of 20), 10.8 μg/ml folic acid, 1.03 mM EDTA, 100 mM Hepes-KOH pH 7.6/30° C., 1

μg/ml rifampicin, 0.03% sodium azide, 40 mM acetyl phosphate, 480 μg/ml tRNA from *E. coli* MRE600, 2 mM dithiothreitol, 10 mM MESNA (mercaptoethane sulfonic acid), 70 mM potassium hydroxide, 0.1 U/μl RNase inhibitor, 15 μg/ml plasmid, 220 μl/ml *E. coli* A19 lysate, 2 U/μl T7 RNA polymerase.

Supply solution: 185 mM potassium acetate, 15 mM magnesium acetate, 4% glycerol, 2.06 mM ATP, 1.02 mM CTP, 1.64 mM GTP, 1.02 mM UTP, 257 μM of each amino acid (a total of 20), 10.8 μg/ml folic acid, 1.03 mM EDTA, 100 mM Hepes-KOH pH 7.6/30° C., 1 μg/ml rifampicin, 0.03% sodium azide, 40 mM acetyl phosphate, 2 mM dithiothreitol, 10 mM MESNA (mercapto-ethane sulfonic acid), 70 mM potassium hydroxide, lysate buffer as described above containing 220 μl/ml.

B. Device

A multi-channel dialyzer in the form of a microtitre plate was used in the example described here. The bottoms of the individual wells of the microtitre plate were each provided with a dialysis membrane with a cut off volume of 10 kilodaltons. The maximum reaction volume per well was 200 μl. The housing for the supply solution had a capacity of 200 ml.

C. Movement, Cover

Shaking device: Flow laboratories, type: Titertek® with a shaking frequency step 4.5

Incubation hood: Edmund Buihler, type: TH25, at a temperature of 30° C.

D. Procedure

Separate reaction mixtures of the above-mentioned composition were pipetted:
1) for the expression of GFP containing pM-GFP or pIVEX-GFP
2) for the expression of CAT containing pHM-CAT A volume of 8.4 ml was prepared for each mixture and 200 μl thereof was pipetted into a total of 40 wells (0.4 ml as excess) i.e. 40 wells per mixture and protein. 200 ml supply solution of the above-mentioned composition was pipetted for the supply chamber, i.e. a common supply solution was used for both reaction mixtures. After sealing the microtitre plate with an adhesive foil, the device was attached to the shaking device which was located under the incubation hood. After adjusting the shaking frequency and the incubation temperature of 30° C., the reaction mixtures were incubated for 20 hours.

E. Evaluation

1. Expression of GFP

The samples were measured using a spectral fluorimeter from the Kontron Company, type: TEGIMENTA, SFM25. Excitation was at a wavelength of 395 nm. Emission rate at 580 to 430 nm. Emission maximum is at 510 nm. rGFP (recombinant GFP) from Roche Diagnostics, Catalogue number 1814524 was used as the standard. The samples were diluted 1:200 with the lysate buffer and the standard was diluted to 1 μg/ml and 2 μg/ml. In Table 1, 10 values from the 40 obtained (which were all in the same range) are shown as a representative selection.

Figure 1:
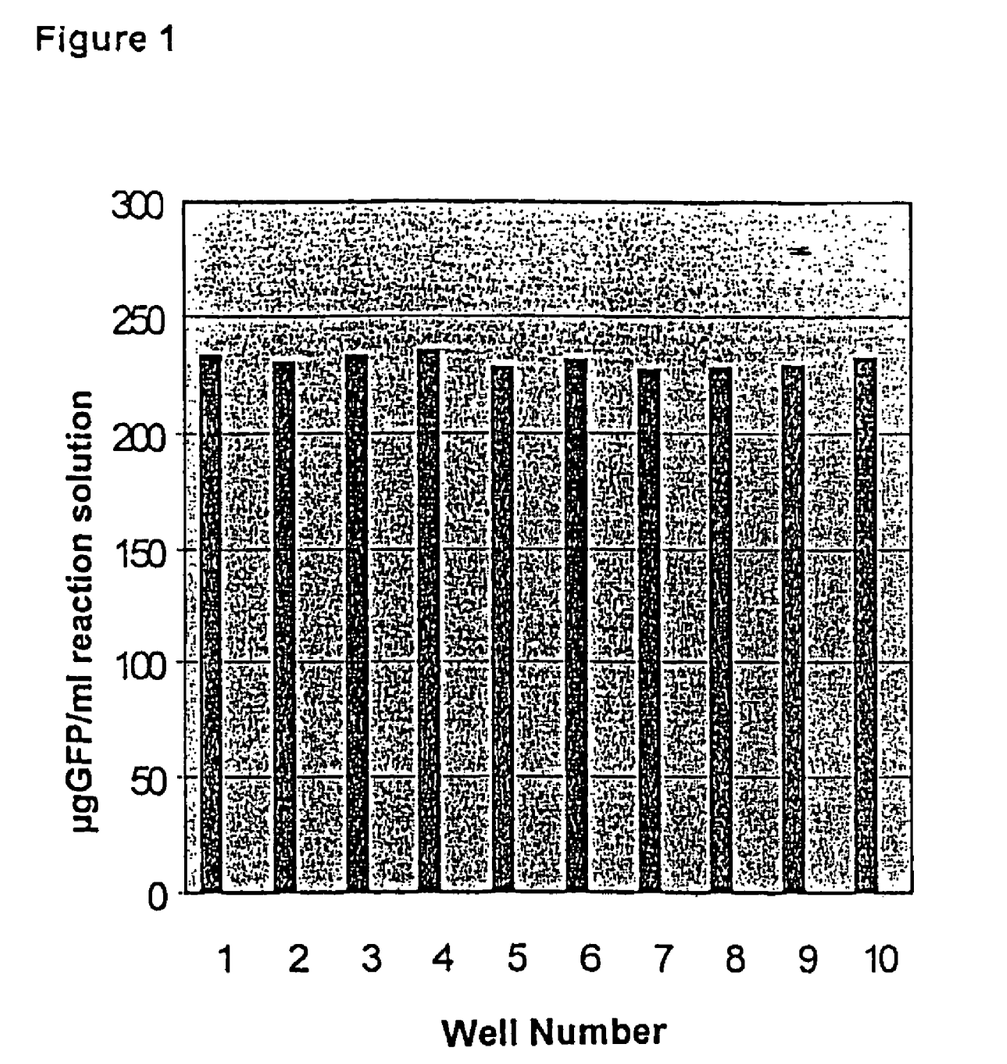
FIG. 1 shows a graphic evaluation of the values shown in Table 1 in μg GFP/ml reaction solution in the selected wells.

FIG. 1 shows a graphic evaluation of the values shown in Table 1 in μg GFP/ml reaction solution in the selected wells.

TABLE 1

| well number | 1 | 2 | 3 | 4 | 5 | 6 | 7 | 8 | 9 | 10 |
|---|---|---|---|---|---|---|---|---|---|---|
| μg GFP/ml reaction volume | 366 | 365 | 362 | 356 | 369 | 371 | 365 | 367 | 361 | 365 |

2. Expression of CAT

The samples were measured by HPLC analysis using the instrument type: LKB 2150. A CAT enzyme from Roche Diagnostics, Catalogue number 1485156 was used as a standard.

In Table 2, 10 volumes from the 40 obtained (which were all in the same range) are shown as a representative selection.

Figure 2:
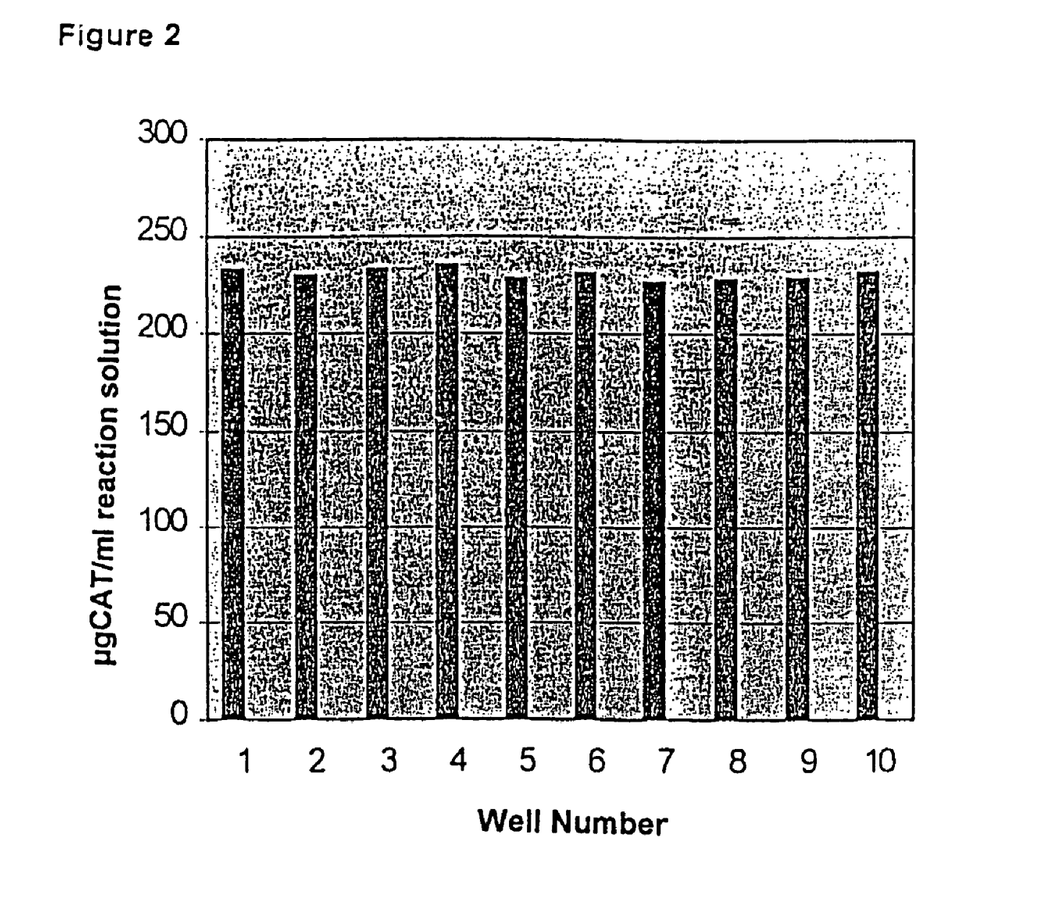
FIG. 2 shows a graphic evaluation of the values shown in Table 2 in μg CAT/ml reaction solution in the selected wells.

FIG. 2 shows a graphic evaluation of the values shown in Table 2 in μg CAT/ml reaction solution in the selected wells.

TABLE 2

| well number | 1 | 2 | 3 | 4 | 5 | 6 | 7 | 8 | 9 | 10 |
|---|---|---|---|---|---|---|---|---|---|---|
| μg CAT/ml reaction solution | 233 | 230 | 233 | 235 | 228 | 231 | 227 | 228 | 229 | 232 |

The invention claimed is:

1. A high throughput device for concurrent in vitro protein synthesis of multiple proteins, said device comprising

9 an inner housing;
an external housing for receiving said inner housing, wherein
said inner housing comprises
  a reaction block having a plurality of chambers formed therein, each chamber being in fluid communication with the top and bottom surface of said reaction block via a first port and a second port, respectively;
  a first and second semipermeable membrane covering said first and second ports, respectively;
  a producing system for said synthesis, said producing system held within the plurality of chambers between said first and second semipermeable membranes; and
  a supply block having a plurality of chambers formed therein, each supply block chamber being in fluid communication with the top and bottom surface of said supply block via a third port and a fourth port, respectively;
wherein said bottom surface of the supply block is held in contact with the first semipermeable membrane and the chambers of the supply block are aligned with the chambers of the reaction block, placing the individual chambers of the reaction block and the supply block in fluid communication by passage through the first semipermeable membrane;
wherein said external housing and said chambers of the supply block hold a supply liquid for said synthesis, said supply liquid being separated from the producing system by said first and second semipermeable membranes;
means for mixing the producing systems and the supply liquid simultaneously, wherein said means are functionally coupled to the device, and
means for incubating the producing systems and the supply liquid.

2. The device of claim 1 wherein each reaction block chamber has a volume between 50 µl and 10 ml.

3. The device of claim 1 wherein the supply liquid contained in said external housing has a volume that is five to twenty times the sum of the volumes of the reaction block chambers, and the supply liquid in each supply block chamber has a volume that is five to twenty times the volume of each respective reaction block chamber.

4. The device of claim 3 wherein said first and second semipermeable membrane each have a pore size of 3 to 100 kDa.

5. The device of claim 4 wherein said first and second semipermeable membrane each have a pore size of 10 to 14 kDa.

6. The device of claim 1 wherein the external housing is sealed with a cover.

7. The device of claim 1 wherein the bottom surface of said reaction block further comprises a plurality of vertical projections extending around the perimeter of each of said second ports and extending away from the bottom surface to form a well, wherein distal end of the well is attached to said second permeable membrane.

8. The device of claim 7 wherein said inner housing further comprises a plurality of supply chambers wherein each supply chamber is formed for receiving only a subset of the plurality of wells and each supply chamber is only in fluid communication with the subset of the plurality of wells received by the supply chamber.

9. The device of claim 1 wherein the means for mixing comprises a shaking device.

10

10. A high throughput device for concurrent in vitro protein synthesis of multiple proteins, said device comprising
an inner housing;
an external housing for receiving said inner housing, wherein
said inner housing comprises
  a reaction block having a plurality of chambers formed therein, each chamber being in fluid communication with the top and bottom surface of said reaction block via a first port and a second port, respectively, wherein the side walls of the chambers of said reaction block are coated with a component which specifically binds the synthesized protein;
  a first and second semipermeable membrane covering said first and second ports, respectively;
  a producing system for said synthesis, said producing system held within the plurality of chambers between said first and second semipermeable membranes; wherein said external housing holds a supply liquid for said synthesis, said supply liquid being separated from the producing system by said first and second semipermeable membranes;
means for mixing the producing systems and the supply liquid simultaneously, wherein said means are functionally coupled to the device, and
means for incubating the producing systems and the supply liquid.

11. The device of claim 10 wherein the component is selected from the group consisting of streptactin, avidin, or streptavidin.

12. A method for concurrent in vitro synthesis of multiple proteins comprising
providing a high throughput device comprising an external housing that encloses an inner housing, the inner housing comprising
  a reaction block having a plurality of chambers formed therein, each chamber being in fluid communication with the top and bottom surface of said reaction block via a first port and a second port, respectively; and
  a first semipermeable membrane covering said second port;
connecting the device to means for mixing and incubating,
providing a cell-free protein biosynthesis solution to each of said plurality of chambers,
sealing the plurality of first ports of each chamber with a second semipermeable membrane,
placing the inner housing in said external housing and contacting the first and second semipermeable membranes with a supply liquid under conditions such that the molecular exchange takes place by diffusion, wherein the volume of the supply liquid is added in an amount ten times the total volume of the cell-free protein biosynthesis solution,
mixing the cell-free protein biosynthesis solution and the supply liquid simultaneously,
incubating the cell-free protein biosynthesis solution at a constant temperature between 20° C. and 37° C. to initiate protein synthesis.

13. A high throughput device for concurrent in vitro protein biosynthesis of multiple proteins, said device comprising
an inner housing;
an external housing for receiving said inner housing, wherein said inner housing comprises
  a reaction block having a plurality of chambers formed therein, each chamber being in fluid communication with the top and bottom surface of said reaction block via a first port and a second port, respectively; and a first and second semipermeable membrane covering said first and second ports, respectively, wherein the bottom surface of said reaction block further comprises a plurality of vertical projections extending around the perimeter of each of said second ports and extending away from the bottom surface to form a well, wherein distal end of the well is attached to said second permeable membrane.

14. The device of claim 13 wherein said inner housing further comprises a plurality of supply chambers wherein each supply chamber is formed for receiving only a subset of the plurality of wells and each supply chamber is only in fluid communication with the subset of the plurality of wells received by the supply chamber.

15. The device of claim 13 wherein the inner housing further comprises a supply block having a plurality of chambers formed therein, each supply block chamber being in fluid communication with the top and bottom surface of said supply block via a third port and a fourth port, respectively, wherein said bottom surface of the supply block is held in contact with the first semipermeable membrane and the chambers of the supply block are aligned with the chambers of the reaction block, placing the individual chambers of the reaction block and the supply block in fluid communication by passage through the first semipermeable membrane.

* * * * *